(12) United States Patent
Warner et al.

(10) Patent No.: US 6,610,156 B2
(45) Date of Patent: *Aug. 26, 2003

(54) METHOD FOR RECOVERY OF NITRAMINES FROM ALUMINIZED ENERGETIC MATERIALS

(75) Inventors: Kirstin F. Warner, Ogden, UT (US); Louis F. Cannizzo, North Ogden, UT (US); Robert M. Hajik, Willard, UT (US)

(73) Assignee: Alliant Techsystems Inc., Edina, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 09/784,476

(22) Filed: Feb. 15, 2001

(65) Prior Publication Data

US 2003/0111148 A1 Jun. 19, 2003

Related U.S. Application Data

(60) Provisional application No. 60/188,182, filed on Mar. 10, 2000.

(51) Int. Cl.[7] .............................................. C06B 33/08
(52) U.S. Cl. ....................................................... 149/74
(58) Field of Search ............................ 588/203; 149/74

(56) References Cited

U.S. PATENT DOCUMENTS

| | | | |
|---|---|---|---|
| 4,098,627 A | 7/1978 | Tompa et al. | |
| 4,231,822 A | 11/1980 | Roth | |
| 4,389,265 A | 6/1983 | Tompa et al. | |
| 4,661,179 A | 4/1987 | Hunter et al. | |
| 4,713,232 A | 12/1987 | Chin et al. | |
| 4,909,868 A | 3/1990 | Melvin | |
| 5,011,614 A | 4/1991 | Gresser et al. | |
| 5,221,486 A | 6/1993 | Fassbender | |
| 5,284,995 A | 2/1994 | Melvin | |
| 5,430,229 A | 7/1995 | Voss | |
| 5,434,336 A | 7/1995 | Adams et al. | |
| 5,445,690 A | 8/1995 | Wulfman | |
| 5,763,736 A | 6/1998 | Daume | |
| 6,011,193 A | 1/2000 | Myler et al. | |
| 6,063,960 A | 5/2000 | Phillips et al. | |
| 6,414,143 B1 * | 7/2002 | Cannizzo et al. | 149/124 |
| 6,416,601 B1 * | 7/2002 | Warner et al. | 540/475 |

OTHER PUBLICATIONS

Recovery of HMX from Scrap PBX–9404 High Explosive, Technical Report 219, by Ernest E. Leake AEC Operations Division, Oct. 26, 1973.

\* cited by examiner

*Primary Examiner*—John Hardee
(74) *Attorney, Agent, or Firm*—TraskBritt

(57) ABSTRACT

Nitramines are one of the more expensive and often the more plentiful ingredients found in energetic materials, such as solid rocket motor propellants, explosives, and pyrotechnics. By treating aluminized energetic material with an aqueous nitric acid solution containing not more than 55% by weight aqueous nitric acid at a weight ratio of aqueous nitric acid to energetic material of about 4:1 to about 6:1, most constituents of conventional aluminized energetic materials are digested into solution, with the exception of nitramines, which remain substantially insoluble in the aqueous nitric acid and can be recovered without requiring recrystallization of the nitramines. A mineral acid other than nitric acid, preferably hydrochloric acid, may be added to increase the rate of aluminum digestion. Treatment of the energetic material can be performed without volatile organic solvents, thus obviating ecological, cost, and safety concerns raised by the use of volatile organic solvents.

21 Claims, 1 Drawing Sheet

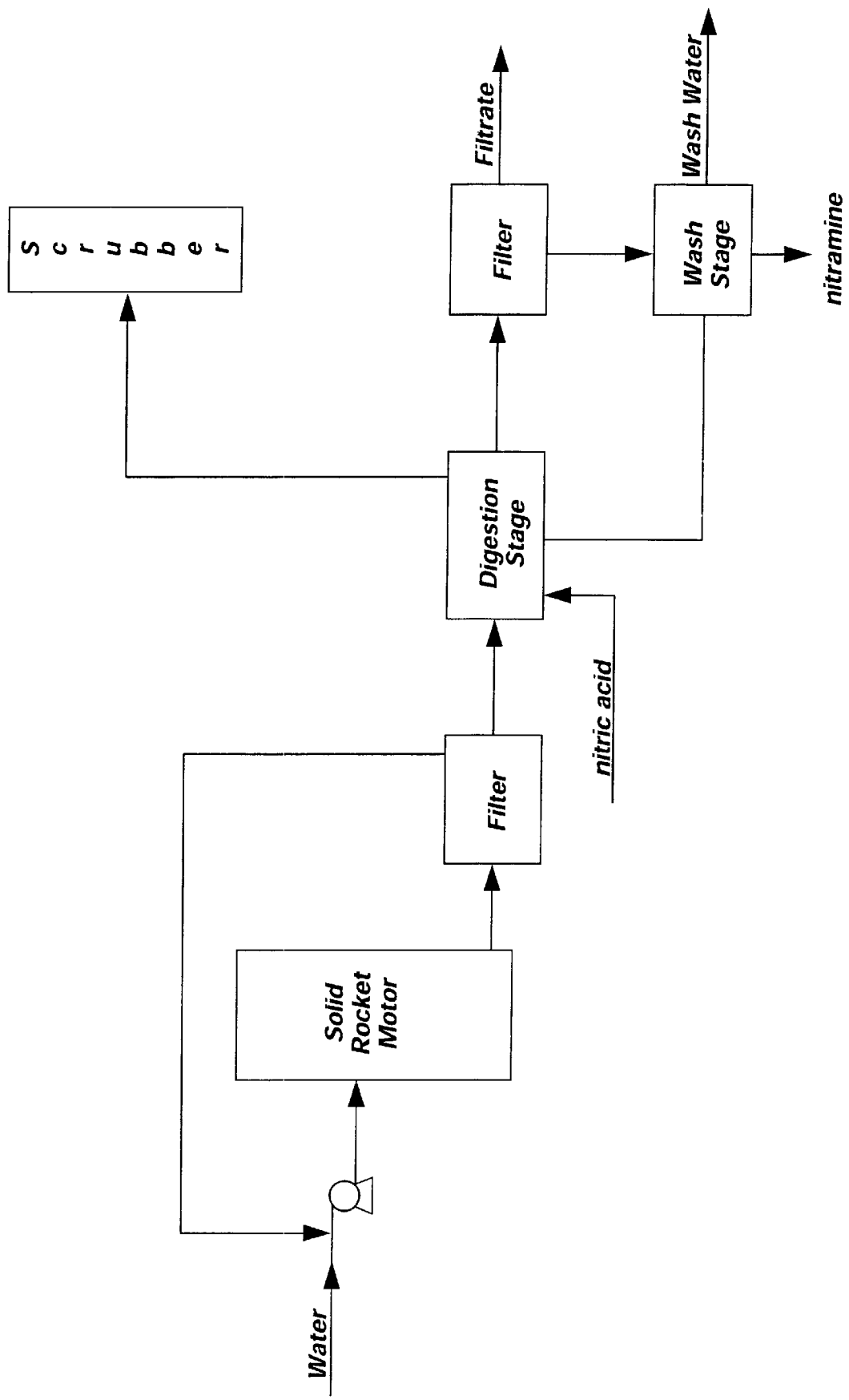

METHOD FOR RECOVERY OF NITRAMINES FROM ALUMINIZED ENERGETIC MATERIALS

CROSS-REFERENCE TO RELATED APPLICATION

This application claims the benefit of filing of U.S. provisional application No. 60/188,182 filed in the U.S. Patent & Trademark Office on Mar. 10, 2000. The complete disclosure of provisional application 60/188,182 is incorporated herein by reference. In the event that any portion of the provisional application is inconsistent with this application, this application supercedes the provisional application.

BACKGROUND OF THE INVENTION

Field of the Invention: This invention relates to the recovery of nitramines from aluminized energetic materials. This invention is particularly useful for recovering nitramines from aluminized energetic materials such as solid propellants, explosives, and pyrotechnics.

State of the Art: Energetic materials have found widespread use, perhaps no more extensively than in military applications, where energetic materials are used to make composite propellants for ballistic missiles and explosive compositions for munitions and ordnances. An example of a propellant commonly found in rocket motors and missiles is Class 1.1 solid propellants. Like most other energetic materials used in military applications, Class 1.1 solid propellants are formed from a composition comprising a combination of one or more of the following: polymeric binders, plasticizers, ballistic additives, chemical stabilizers, curing agents and catalysts, metal powders, and inorganic and/or organic oxidizers.

Demilitarization in the United States and abroad has created a need for an economical, reliable, non-hazardous, and environmentally friendly method for disposing of the stockpile of surplus tactical missiles and explosives existing worldwide. Additionally, a growing number of larger rocket motors, such as intercontinental ballistic missiles (ICBMs), are being and will have to be demilitarized due to international treaties, such as the START treaties. The disposal of such energetic materials is the subject of various publications and U.S. patents, including U.S. Pat. No. 4,231,822 to Roth and U.S. Pat. No. 4,661,179 to Hunter et al. However, these U.S. patents focus on disposing of explosive materials by "desensitizing" or "destroying" the materials.

The degradation of energetic materials into an unusable state is not the most economical alternative of disposal, since many energetic materials are both expensive and reusable. For example, one class of organic oxidizer that has found wide acceptance in the rocket propulsion, explosive; and pyrotechnic arts comprises nitramines. Common nitramines include, for example, cyclotetramethylenetetranitramine (also known as HMX and 1,3,5,7-tetranitro-1,3,5,7-tetraaza-cyclooctane), cyclotrimethylenetrinitramine (also known as RDX and 1,3,5-trinitro-1,3,5-triaza-cyclohexane), TEX (4,10-dinitro-2,6,8,12-tetraoxa-4,10-diazatetracyclo-[5.5.0.0$^{5,9}$0$^{3,11}$]-dodecane), HNIW (also known as CL-20) (2,4,6,8,10,12-hexanitro-2,4,6,8,10,12-hexaazatetracyclo [5.5.0.0$^{5,9}$0$^{3,11}$]-dodecane), and combinations thereof. Nitramines are commonly among the most expensive and highly energetic ingredients of conventional energetic compositions. Further, nitramines are sometimes present in energetic compositions in relatively high concentrations, such as on the order of up to about 50% by weight of solid rocket motor propellants and up to about 98% by weight of explosives. These factors make the successful and efficient recovery of nitramines in high yields for subsequent re-use highly desirable.

A method for the extraction and recovery of nitramine oxidizers from solid propellants is disclosed in U.S. Pat. No. 5,284,995 to Melvin, which discloses the use of a liquid ammonia extraction agent for extracting the nitramines HMX and RDX from rocket motor solid propellants. The use of liquid ammonia in nitramine recovery techniques introduces several complexities and expenses, especially in a closed system, including high capital expenditures required as outlay to obtain equipment capable of operating at the high-pressures (5 to 40 Kpsi) at which liquid ammonia is handled. The presence of liquid ammonia also creates other problems, such as worker safety issues, since contact between the ammonia and human skin can cause severe chemical burns to the handler. Additionally, liquid ammonia is combustible, and presents a severe inhalation hazard if not handled correctly. Another disadvantage of the U.S. Pat. No. 5,284,995 process is that subjecting energetic materials, such as Class 1.1 propellants containing nitramine oxidizers, to the pressurized environments described in the '995 patent increases the risk of accidental detonation, as well as the accompanying catastrophic consequences that an accidental detonation or explosion often has on human life and property. Yet another disadvantage of the process of U.S. Pat. No. 5,284,995 is that nitramines are dissolved in liquid ammonia, requiring recrystallization of the nitramines. However, the recrystallized nitramines have different particle sizes than the nitramine particles found in the propellant. Also, if recrystallization is not performed under the right conditions, the polymorph of the nitramine changes during recrystallization.

Another method for recovering ingredients from a pyrotechnic material is disclosed in U.S. Pat. No. 4,098,627 to Tompa et al., in which the pyrotechnic containing a cured polymeric binder is decomposed under mild conditions. The method involves heating the pyrotechnic material to a temperature of from about 50° C. to about 160° C. in a liquid medium comprising an active hydrogen-containing compound capable of cleaving the chemical bonds contained in the polymer. Representative liquid media include mineral acids such as hydrochloric acid, sulfuric acid, phosphoric acid, nitric acid and perchloric acid, as well as primary amines, secondary amines, ammonia, and water. The process is expedited by modifying the liquid medium via the addition of an organic solvent. Organic solvents reportedly suitable in the process are toluene, xylene, dioxane, and tetrahydrofuran. The organic solvent functions either to swell the organic polymeric binder present in the pyrotechnic material or to dissolve filler material present in the pyrotechnic material. The decomposition technique is carried out at 80° to 120° C. In practice, however, these organic solvents raise a host of ecological and safety concerns, including flammability, VOC emissions, environmentally sound and cost-effective waste disposal, and handling expenses. Additionally, U.S. Pat. No. 4,389,265 to Tompa et al. reports that the use of mineral acids and water in the manner prescribed by the '627 patent produces low yields of about 36%. Indeed, example 5 of the '627 patent reports that under the basic conditions of its process RDX may be destroyed.

Two additional approaches for reclaiming nitramines from propellants having polymeric binders are disclosed in U.S. Pat. No. 4,389,265 to Tompa et al. The first approach utilizes a solution of 2-aminoethanol in a mixture of an aromatic solvent and an alcohol to dissolve the propellant binder. The 2-aminoethanol breaks down or dissolves the polymeric binder. Examples of aromatic solvents suitable for the first approach include benzene, toluene, xylene, ethylbenzene, and diethylbenzene. Examples of alcohols suitable for the first approach include ethanol, 1-propanol, 2-propanol, and mixtures thereof. The second approach is performed with a solution of a mineral acid other than nitric acid, an organic solvent, and water. For the second approach, examples of suitable mineral acids are hydrochloric, sulfuric and phosphoric acid; examples of organic solvents are acetone, methylethylketone, tetrahydrofuran, and mixtures thereof. The mineral acid and organic solvent combine to break down or dissolve the polymeric binder. After dissolution of the pyrotechnic binder is completed in the 2-aminoethanol or the mineral acid process, the nitramine and metals, if present, are removed by filtration and the nitramine is extracted in acetone. Although relatively high yields are reported in U.S. Pat. No. 4,389,265, the presence of aromatic and organic solvents raises ecological and safety concerns over such issues as flammability, volatile emissions, and waste disposal. Also, the nitramine is recovered with aluminum fuel particulates. Consequently, separation of the aluminum requires dissolving, filtering, and recrystallizing of the nitramine. As mentioned above, recrystallization can cause the polymorph and size of the nitramine particles to change.

U.S. Pat. No. 6,063,960 discloses the recovery of nitroamines and reformulation of by-products. The '960 patent generally focuses on non-aluminized propellants, with the exception of its mention of VTG-5A and WAY, both of which are aluminized propellants. According to the '960 patent, the propellants are treated with 60–70% nitric acid in a preferred ratio of nitric acid solution to feed of 1.0:1.0 l/kg. This feed ratio calculates to a weight ratio of less than 1.5:1. Although these conditions are adequate to recover nitramines from non-aluminized propellants containing conventional binders, in the case of an aluminized propellant a substantial proportion of aluminum would not be dissolved under these conditions. Accordingly, in the event that an aluminized propellant were treated by the '960 process, separation of the aluminum would require additional steps of dissolving, filtering, and recrystallizing of the nitramine.

Thus, it would be a significant improvement in the art to develop a method in which nitramines are recovered from aluminized energetic materials without recrystallizing the nitramines and in which there is no need for the use of either liquid ammonia under increased pressure or hazardous organic solvents that are volatile and/or flammable.

BRIEF SUMMARY OF THE INVENTION

The present invention fulfills a long-felt need in the art by providing a nitramine-recovery process capable of achieving the above-discussed improvements in the recovery of nitramines from aluminized energetic materials, especially aluminized propellants, without relying upon either the use of liquid ammonia under increased pressures or the application of hazardous solvents.

In accordance with the principles of this invention, a nitramine-recovery process is provided in which a nitramine-containing aluminized energetic material is treated with aqueous nitric acid having a nitric acid concentration of not more than 55% by weight. This low concentration nitric acid, when used in appropriate ratios relative to the aluminized energetic material to be treated, has the effect of digesting by solvation and/or solvolysis most, if not all, conventional ingredients other than nitramines commonly found in aluminized energetic materials. As referred to herein, the term solvation means the dissolving of a solid into a solvent without chemical reaction. As also referred to herein, the term solvolysis means the dissolving of a solid into a solvent via chemical reaction between the solid and solvent. The nitramines remain substantially insoluble (i.e., are neither solvated nor solvolyzed) in the low concentration nitric acid, and can be separated from the aqueous nitric acid and digested ingredients in an efficient manner and without incurring great expense. The recovered nitramines according to the presently preferred embodiment are suitable for recycling into an energetic material, including a solid propellant grain, explosive material, and pyrotechnics (known in the art as PEP materials).

There are several advantages that can be derived from the inventive process. For example, nitramine yields associated with embodiments of the present invention have been found to be much higher than most conventional processes. In particular, nitramine yields are routinely on the order of 90% by weight or greater according to embodiments of the inventive process. Further, the process can be performed, and preferably is performed, free of organic solvents, thus avoiding the ecological and safety concerns and waste disposal and handling expenses of conventional processes. Furthermore, the digested ingredients separated from the nitramine can be recovered and reused as feed stock for commercial blasting agents, thus further reducing the waste disposal concerns and improving the efficiency of the process. The process also does not require volatile digestion agents or high pressurizes that increase the risk of unintentional detonation of the energetic material.

The recovery method of this invention is particularly useful for recovering nitramines from aluminized energetic materials such as solid propellants, explosives, and pyrotechnics, and is especially useful for the recovery of nitramines from aluminized solid rocket motor propellants. While not wishing to be bound by any theory, it is believed that unlike many conventional methods, in which nitramines are typically dissolved in order to separate the nitramines from aluminum and/or other ingredients, in the present invention the aluminum reacts with aqueous nitric acid to form aluminum nitrate $Al(NO_3)_3 \cdot 9H_2O$, which is soluble in the aqueous nitric acid and may be separated from the substantially insoluble nitramine. Additionally, unlike other inorganic acids that react with aluminum to rapidly generate large amounts of hydrogen gas and high temperatures, nitric acid has been found to undergo a much more sedate reaction with aluminum. The reaction of nitric acid with aluminum generates hydrogen gas and heat at manageable rates so as to permit the hydrogen gas and heat to be removed from the digestion vessel.

However, it has been found that the slowest part of the nitramine-recovery process is the digestion of the aluminum present in the energetic material.

Therefore, the invention according to another aspect provides a modification to the above-described inventive nitramine-recovery, process by which the aluminum may be digested at a more efficient rate.

In accordance with the principles of this aspect of the invention, at least one mineral acid other than nitric acid is added to the digestion process. It is also preferred that the addition of the mineral acid be delayed until sufficient time has passed for the aqueous nitric acid to digest the binder of the energetic material. The time needed for digesting the binder will depend upon several factors, including the amount of binder in the energetic material, the concentration and amount of aqueous nitric acid, and process conditions, such as temperature. Suitable mineral acids include hydrochloric acid, perchloric acid, sulfuric acid, phosphoric acid, hydrobromic acid, hydroiodic acid. Hydrochloric acid is currently preferred because of its high rate of aluminum digestion. Representative concentrations of mineral acid for use in the aluminum digestion range, for example, from about 1 part by weight to about 5 parts by weight based on 100 parts by weight of the aqueous nitric acid. Such concentrations are usually sufficient to digest at least 99 weight percent of the aluminum. Aqueous nitric acid is preferably not selected as the mineral acid for aluminum digestion. Nitric acid is relatively oxidizing compared to other mineral acids, and will oxide the surface of the aluminum to form aluminum oxide, thereby slowing the rate at which the aluminum is digested. The use of additional mineral acid facilitates and accelerates aluminum removal.

Other aspects and advantages of this invention will become more apparent to those skilled in the are upon reading the specification and appended claims which, when read in conjunction with the accompanying drawing, explain the principles of this invention.

BRIEF DESCRIPTION OF THE DRAWING

The accompanying Figure serves to elucidate the principles of this invention by illustrating a flow diagram for the extraction and recovery of nitramines from energetic materials in accordance with an embodiment of this invention.

DETAILED DESCRIPTION OF THE INVENTION

Among nitramine-containing aluminized energetic materials that can be successfully treated to recover nitramines are solid rocket motor propellants. Although the method of this invention is particularly well suited for aluminized solid rocket motor propellants, the inventive method can also be applied to other materials, such as minimum smoke propellants and reduced smoke propellants containing little or no aluminum. The inventive method finds applicability to a wide array of propellants and propellant binders. For example, the method can be used to recover nitramines from composite propellants, modified composite propellants, double-base propellants, crosslinked double-base propellants, and other plasticized and non-plasticized propellants. As mentioned above, the present invention is not restricted to recovery of nitramines from propellants; instead, the invention finds applicability to other energetic materials, including other PEP (propellant, explosive, and pyrotechnic) materials, such as plastic bonded explosives (PBX), melt cast explosives, and slurried explosives. Although the inventive process can be applied to energetic materials containing both high and low concentrations of nitramines, it is most economical to apply the inventive process to energetic materials containing at least about 10% by weight nitramine. Representative nitramines that can be recovered by the present invention include HMX, RDX, CL-20, and TEX.

Referring now more particularly to the Figure, there is shown an embodiment of the present invention in which nitramines are recovered from a solid rocket motor assembly. In particular, a rocket motor case containing a propellant, such as a Class 1.1 solid propellant grain, is provided for the recovery process. In the illustrated embodiment, the propellant is removed from the rocket motor case by passing water through a pump or series of pumps to create high pressure water, which is jetted into the rocket motor case and directed through appropriate nozzles at the propellant to cut the propellant from the rocket motor case. Generally, water pressures of about 10,000 psi will suffice to remove the propellant from the rocket motor case. The selection of suitable pumps, valves, and jets to effect removal of the propellant from the rocket motor case is within the purview of those skilled in the art and, for this reason, is not discussed in greater detail herein. It is to be understood, however, that the present invention is not limited to the removal of energetic material from its housing by the use of high pressure water or other hydraulic treatments. To the contrary, other mechanical and chemical methods can be selected and applied to remove the energetic material from its housing or case.

In the illustrated embodiment, the propellant and water are collected and passed to a filter, where a portion of the water used to remove the propellant from the rocket motor case is recycled back to the pump.

The propellant and the remaining amount of water (not recycled to the hydraulic removal stage), if any, then enter into a digestion stage, where the propellant is treated with aqueous nitric acid. The propellant entering into the digestion stage preferably is present in relatively small pieces. For example, it is preferred that the largest dimension of the propellant pieces be no larger than about 2.54 cm (1 inch), more preferably no larger than 1.27 cm (0.5 inch). Generally, it is most efficient to extract the propellant from the rocket motor case in such a manner that the extracted propellant has the desired dimensions. Alternatively, the propellant can be subjected to a milling or grinding step or the like (not shown) before the propellant enters the digestion stage.

One of the important aspects of this invention resides in treating the nitramine-containing propellant with a digestion agent comprising a dilute aqueous nitric acid solution characterized by not more than 55% by weight nitric acid. Because the aqueous nitric acid digestion agent is relatively dilute, substantially all of the nitramine charged into the digestion stage neither solvates nor solvolyzes in the digestion stage, but is removed from the digestion stage as a solid. As referred to herein, substantially all means that at least 95% by weight of the nitramine is not digested in the digestion stage, although preferably at least 98% by weight, and more preferably at least 99% by weight of the nitramine in the energetic material is not digested in the digestion stage. The amount of nitramine that is digested (by solvation and/or solvolysis) into the aqueous nitric acid depends not only on the concentration of the aqueous nitric acid solution, but also on the ratio of nitric acid to propellant. Generally, desirable results can be obtained by setting the weight ratio of aqueous nitric acid solution to propellant to be in a range of from about 1:1 to 6:1, although this range is not exhaustive as to the scope of this invention. The weight ratio of aqueous nitric acid solution to propellant will generally be higher for aluminized propellants than for non-aluminized propellants. For example, the weight ratio of aqueous nitric acid solution to propellant for treating aluminized propellant is preferably in a range of from about 4:1 to about 6:1, still more preferably about 5.3:1.

Although the aqueous nitric acid solution used in the inventive process is sufficiently dilute to avoid digestion of substantially all of the nitramine, the aqueous nitric acid solution is able to digest into solution, by solvation and/or solvolysis, most if not all of the remaining ingredients of the energetic material. For example, nitrate ester plasticizers are solvolyzed by hydrolyzing the plasticizers with nitric acid to form alcohol, which further decomposes into water and carbon dioxide. Polymeric binders, stabilizers, and other organic ingredients also are digested by hydrolysis in aqueous nitric acid. Inorganic oxidizers such as ammonium perchlorate, potassium perchlorate, 1-ammonium nitrate, hydroxyl ammonium nitrate, and potassium nitrate, are soluble in aqueous nitric acid, and solvated into the aqueous nitric acid.

The rate at which the aqueous nitric acid solution digests the energetic material ingredients (other than the nitramines), as well as the amount of nitramines (if any) that is digested into solution, depend on several factors, including the concentration of the aqueous nitric acid solution and the temperature at which digestion occurs. The concentration of the aqueous nitric acid solution should not be more than 55% by weight, but preferably is at least 5% by weight, more preferably at least 20% by weight, and still more preferably at least 35% by weight concentration in order to drive the digestion reaction at an acceptably fast rate. Digestion can occur within a temperature range of from about room temperature (or slightly lower) to the boiling point of the aqueous nitric acid. It is preferred to carry out the digestion within a temperature range of from about 30° C. to about 90° C., more preferably about 30° C. to about 80° C.

In the illustrated embodiment, nitric acid fed via its own feed stream into the digestion stage may be concentrated or diluted. In the event that concentrated nitric acid is fed into the digestion stage via the nitric acid feed stream, water for diluting the nitric acid to an acceptable concentration (of not more than 55% by weight) can be supplied via the water entering with the propellant from the filter and/or via water supplied in a recycle stream from a final wash stage (discussed below). Although not shown, either of these streams and/or another water-supply stream can combine with the nitric acid prior to entering into the digestion stage.

During the digestion process, nitric oxides ($NO_x$) can be generated, sometimes in significant quantities. The nitric oxides generated during digestion can be removed from the digestion vessel by conventional means, such as, for example, a $NO_x$ scrubber. Hydrogen is also generated during the process, although at relatively slow rates compared to processes using other mineral acids. The hydrogen gas should be monitored and vented to reduce the risk of unintentional explosion.

In order to facilitate aluminum digestion, a mineral acid other than nitric acid may be added into the solution to digest at least a portion of the aluminum, and in a preferred embodiment at least 99 weight percent of the aluminum. Suitable mineral acids include, for example, one or more of the following: hydrochloric acid, perchloric acid, sulfuric acid, phosphoric acid, hydrobromic acid, and hydroiodic acid. Hydrochloric acid is currently the mineral acid of choice. The mineral acid may be added in a range of about 1 to about 50 parts by weight per 100 parts by weight of the aqueous nitric acid.

In accordance with the preferred version of the invention, a slurry of nitramine in the digested liquid solution and the residual aqueous nitric acid is then sent to a separator, such as a filter, where filtration can be performed using suitable liquid/solid separation techniques, such as, for example, filter pressing or centrifugal separation. The filtrate contains large amounts of nitrates, metal fuels, and oxidizers, and can be used as an ingredient for a commercial blasting agent. The nitramine is sent to a wash stage for washing with water. The water may be filtered and sent to the digestion stage, as shown in the illustrated embodiment. Yields of nitramine of more than 90% by weight, and often more than 95% by weight, can be realized.

The following examples serve to explain embodiments of the present invention in more detail. These examples are not to be construed as being exhaustive or exclusive as to the scope of this invention.

EXAMPLES

Example 1

Into a three-necked 500 mL flask equipped with a mechanical stirrer was added 150 mL of 55 wt % nitric acid and 10.42 grams of size-reduced (1.27cm×1.27 cm×0.32 cm (or ½"×½"×⅛")) propellant pieces containing HMX in a concentration of 53% by weight and, as other ingredients, aluminum powder, polyglycol adipate binder, nitroglycerin plasticizer, ammonium perchlorate oxidizer, nitrate ester stabilizers, and nitrocellullose. The addition of the nitric acid created an initial exotherm, raising the temperature of the mixture to 30° C. The mixture cooled to 25° C. after several minutes, producing a propellant that was completely degraded into powder form after two hours of stirring. The nitroglycerin destruction was monitored by HPLC analysis of the liquid portion of the mixture and recorded as follows (in percent destruction per hours subsequent to start of the process): 77 wt % destruction after 3.7 hours; 85 wt % destruction after 5.7 hours; and 98 wt % destruction after 22.7 hours. After 24 hours, water was added to dilute the initial acid concentration to 35 wt % and stirring continued for another 24 hours. The resulting solid was collected and weighed (5.14 grams) and analyzed by HPLC for HMX concentration (97.1 wt %) and aluminum (2.66 wt % by ICP-AES). The yield of recovered HMX (4.99 grams) was 90% by weight of the original amount of HMX in the propellant.

Example 2

Into a three-necked 500 mL flask equipped with a mechanical stirrer was added 200 mL of 55 wt % nitric acid and 50 grams of size-reduced (1.27cm×1.27 cm×0.32 cm (or ½"×½"×⅛")) propellant pieces containing HMX in a concentration of 53% by weight and, as other ingredients, aluminum powder, polyglycol adipate binder, nitroglycerin plasticizer, ammonium perchlorate oxidizer, nitrate ester stabilizers, and nitrocellullose. The addition of the nitric acid created an initial exotherm, raising the temperature of the mixture to 35° C., where the temperature remained for 24 hours. The propellant that was completely degraded into powder form after two hours of stirring. Nitrogen oxide emissions were observed after 1.6 hours. The nitroglycerin destruction was monitored by HPLC analysis of the liquid portion of the mixture and recorded as follows (in percent destruction per hours subsequent to start of the process): 99.3 wt % destruction after 24 hours; and 99.6 wt % destruction after 28.5 hours. After 29 hours of reaction time, the solid was collected (in an amount of 28.89 grams) and analyzed for HMX (90.2 wt % by HPLC), nitroglycerin (0.025 wt % by HPLC), and aluminum (8.58 wt % by ICP-AES). The yield of recovered HMX was 26.06 grams, or 98% of the amount of HMX present in the original propellant. Further acid digestion of a two gram sample of the collected solid (in 55 wt % nitric acid at 70° C. for 6.0 hours) gave 1.59 grams of white solid. The purified material was analyzed for HMX (100% by HPLC analysis), less than 0.003 wt % nitroglycerin, and 0.009 wt % aluminum.

Example 3

Into a three-liter jacketed wide-mouth flask equipped with a mechanical stirrer was added 1.8 liters of 55 wt % nitric acid. The temperature was adjusted to 24° C. and 450 grams of size-reduced (1.27cm×1.27 cm×0.32 cm (or ½"×½"×⅛")) propellant pieces containing HMX in a concentration of 53% by weight and, as other ingredients, aluminum powder, polyglycol adipate binder, nitroglycerin plasticizer, ammonium perchlorate oxidizer, nitrate ester stabilizers, and nitrocellullose were added over a one-hour period, maintaining the temperature at 24° C. The temperature was maintained at 30–45° C. over the next 28 hours using warm water running through the jacketed flask. The propellant was completely degraded into powder form after two hours of stirring. The nitroglycerin destruction was monitored by HPLC analysis of the liquid portion of the mixture and recorded as follows (in percent destruction per hours subsequent to start of the process): 75.4 wt % destruction after 3 hours; 79.9 wt % destruction after 4 hours; and 87.3 wt % destruction after 5 hours; 94.6% destruction after 7 hours; and 100% destruction after 25 hours. After 29 hours of reaction time, the resulting solid was collected and weighed (246.9 grams) and analyzed by HPLC for HMX concentration (95.0 wt %), nitroglycerin concentration (0.011 wt %), and aluminum (3.87 wt % as measured by ICP-AES). The yield of recovered HMX (234.6 grams) was 98% by weight of the original amount of HMX in the propellant. Further acid digestion of a 206.9 gram sample of the collected solid (in 55 wt % nitric acid at 50C for 24 hours) produced 191.5 grams of pale yellow solid. The purified material was analyzed for HMX content (99.8 wt % by HPLC analysis), nitroglycerin (0.004 wt % by HPLC analysis), and aluminum content (0.0164 wt % by ICP-AES). This represents a projected yield of 228.1 grams, or a 96 wt % recovery from the propellant of HMX. Further analysis of purified material gave the following information: beta polymorph (FTIR), average particle size of 27 micron (Microtracs analysis), 0.044% acetone insoluble, and 0.0289% acidity.

Comparative Example A

A 125 ml Erlenmeyer flask equipped with septum, needle, stir bar, and thermometer was charged with 36 ml of 70 wt. % $HNO_3$. The nitric acid was stirred and heated to 50° C. Over the next six hours a total of 5.0 grams of an aluminized propellant containing about 10 to about 20 wt. % HMX was added in small portions to the heated aqueous nitric acid. The propellant was broken into small pieces less than 0.25 inch (0.64 cm) in diameter, prior to addition. One hour after completion of addition of the propellant, stirring was stopped, and the mixture filtered hot through a coarse frit. The filtrate was diluted with water to 200 ml and allowed to stand overnight. Precipitate was filtered off and dried to give an 81% yield.

Comparative Example B

A double base propellant comprising nitrate esters was pre-treated with hot aqueous ammonia, to destroy the nitrate esters. The resulting powdery residue comprised approximately 25 wt. % HMX, aluminum powder, hydrated alumina, and decomposed binder.

Following the same procedure set forth in Comparative Example A, a total of 2.00 grams of the powdery residue having an average particle size of less than 100 microns was added, except all of the residue was added at once.

The mixture was then stirred and heated at 50° C. for 3 hours. The mixture was filtered hot through a coarse frit. The filtrate was diluted to 200 ml with water and allowed to stand overnight. Precipitate was filtered off and dried to give a 66% yield.

Comparative Example C

A 125 ml Erlenmeyer flask equipped with septum, needle, stir bar, and thermometer was charged with 36 ml of concentrated $HNO_3$. The nitric acid was stirred and heated to 50° C. and 2.000 grams of a PBX explosive, cut into 0.25 inch pieces containing 80–90 wt. % RDX, were added portion-wise over the next hour and a quarter to the acid bath. No change in temperature of the acid bath was observed upon initial addition of the propellant. Upon completion of addition of the propellant, the mixture was heated for an additional 15 minutes, and filtered hot through a coarse frit. The filtrate was diluted with water to 200 ml and allowed to stand overnight. The precipitate was filtered off and dried to give a 68% yield.

Comparative Example D

A 125 ml Erlenmeyer flask equipped with septum, needle, stir bar, and thermometer was charged with 36 ml of concentrated $HNO_3$. The nitric acid was heated to 70° C. and 2.0036 grams of a solid propellant formulation comprising 80–90 wt. % RDX were added portion-wise over the next hour to the acid bath. No change in temperature of the acid bath was observed upon initial addition of the propellant. After all of the propellant was added to the bath, the mixture was heated for another 1.5 hours and then filtered hot through a coarse frit. The filtrate was diluted with water to 200 ml and allowed to stand overnight. The precipitate was filtered off and dried to give a 70% yield.

As demonstrated by the experiments reported above, the use of an aqueous nitric acid solution having a nitric acid concentration of 55 weight percent or less resulted in nitramine recoveries of 90%, 98%, and 96% for Examples 1–3, respectively. By contrast, the use of higher concentrations of nitric acid solution produced lower yields, i.e., 81%, 66%, 68%, and 70% yields for Comparative Examples A–D, respectively.

Examples 4–9

In examples 5–8, 50 grams of a propellant comprising HMX, nitroglycerin, ammonium perchlorate, and aluminum were placed in a three-neck flask with a mechanical stirrer and 400 mL of 55% nitric acid at 80° C. In Example 4, the experiment was scaled up for a 100 gram propellant sample. The propellant was added over 40 minutes. The propellant was heated for 4 hours at 80° C. after final addition of propellant. Concentrated (37 wt %) hydrochloric acid was added to the process for Examples 5–7. Sulfuric acid was added to the process for Example 8. The weight percents of hydrochloric acid and sulfuric acid are based on the parts by weight of the mineral acid per 100 parts by weight of the aqueous nitric acid. (Thus, 5% hydrochloric acid means 5 parts by weight of aqueous hydrochloric acid per 100 parts by weight of aqueous nitric acid.) For Example 9, no additional aluminum digester was added. The sample was worked-up and submitted for analysis. The work-up involved filtering the reaction mixture to isolate the HMX, washing the HMX with water to remove water and impurities from the surface of the HMX, and drying to obtain an accurate recovery weight.

TABLE I

| Example | Al digester | Total Process Time | Temp. (° C.) | wt % of HMX in recovered material* | wt % NG recovered | wt % Al recovered |
|---|---|---|---|---|---|---|
| 4 | 5 wt % HCl at 3.5 hours after final propellant addition | 6.0 hours | 80 | 98 | 0.006 | 0.774 |
| 5 | 1 wt % HCl at 4 hours after final propellant addition | 6.0 hours | 80 | 100 | 0.005 | 0.074 |
| 6 | 1 wt % HCl at 4 hours after final propellant addition | 6.0 hours | 80 | 99 | 0.005 | 0.252 |
| 7 | 1 wt % HCl at 1.5 hours after final propellant addition | 4.5 hours | 84 | 98 | 0.006 | 0.303 |
| 8 | 1 wt % $H_2SO_4$ at 4 hours after final propellant addition | 6.0 hours | 80 | 98 | 0.006 | 1.83 |
| 9 | None | 6.0 hours | 80 | 95 | 0.006 | 4.98 |

*collected solids were subject to HPLC analysis to determine HMX content, with error of ±1 weight percent

Examples 10 and 11

1000 grams of the same propellant used in Examples 4–9 were added at a rate of 20.4 g/min to 55 wt % nitric acid (4.1 L) at 80° C., which took approximately 49 minutes. The propellant was heated for 4 hours at 80° C. An aliquot of solid and acid filtrate was taken for analysis after 4 hours. HCl (277.1 grams) was added drop wise to the reaction mixture, which was heated for another 2 hours at reflux (90° C.) taking an aliquot each hour to monitor the rate of aluminum digestion. The solid was then filtered and an aliquot was taken of the spent acid before the washings. The solid was washed with 4.0 L of water and then oven dried. The total process time including propellant addition was 7.0 hours.

Example 12

528 grams of the same propellant used in Examples 4–9 were added at a rate of 20.4 g/min to 55 wt % nitric acid (2.1 L) at 80° C., which took 25 minutes. The propellant was heated for 2 hours at 80° C. An aliquot of solid and acid filtrate was taken for analysis after 2 hours. HCl (31.68 grams) was added drop wise to the reaction mixture, which was heated for another 2 hours at reflux (90° C.) taking an aliquot each hour to monitor the rate of aluminum digestion. The solid was then filtered and an aliquot was taken of the spent acid before the washings. The solid was washed with 2.0 L of water and then oven dried. The total process time including propellant addition was 4.42 hours.

TABLE II

| Example | Al digester | Process time after propellant addition | wt % of HMX in recovered material* | % NG | % Al | Recovery (%) |
|---|---|---|---|---|---|---|
| 10 | 5% HCl | 6.0 | 100 | 0.007 | None detected | 94 |
| 11 | 5% HCl | 6.0 | 100 | 0.006 | 0.003 | 95 |
| 12 | 1% HCl | 4.0 | 99 | 0.005 | 1.02 | 95 |

*collected solids were subject to HPLC analysis to determine HMX content, with error of ±1 weight percent The foregoing detailed description of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A method of recovering a nitramine from a nitramine-containing aluminized energetic material, said method comprising subjecting the nitramine-containing aluminized energetic material comprising aluminum, a nitramine, and at least one binder to treatment in aqueous nitric acid to digest the binder into solution while neither solvating nor solvolyzing into solution at least substantially all of the nitramine, and recovering at least a portion of the nitramine, wherein a weight ratio of the aqueous nitric acid to the nitramine-containing aluminized energetic material in the treatment is in a range of about 4:1 to about 6:1, and further wherein not more than 55 weight percent of the aqueous nitric acid consists of nitric acid.

2. The method of claim 1, wherein the nitramine-containing aluminized energetic material further comprises at least one plasticizer, and wherein the treatment of the nitramine-containing aluminized energetic material further comprises dissolving the plasticizer into solution.

3. The method of claim 1, wherein the nitramine-containing aluminized energetic material further comprises at least one plasticizer and at least one inorganic oxidizer, and wherein the treatment of the nitramine-containing aluminized energetic material further comprises digesting the plasticizer and the inorganic oxidizer into solution.

4. The method of claim 1, wherein at least 5 weight percent of the aqueous nitric acid consists of nitric acid.

5. The method of claim 1, wherein at least 20 weight percent of the aqueous nitric acid consists of nitric acid.

6. The method of claim 1, wherein at least 35 weight percent of the aqueous nitric acid consists of nitric acid.

7. The method of claim 1, wherein the treatment of the nitramine-containing aluminized energetic material comprises neither solvating nor solvolyzing at least 98% of the nitramine of the nitramine-containing aluminized energetic material into solution.

8. The method of claim 1, wherein the treatment of the nitramine-containing aluminized energetic material comprises neither solvating nor solvolyzing at least 99% of the nitramine of the nitramine-containing aluminized energetic material into solution.

9. The method of claim 1, further comprising using digested portions of the energetic material and residual nitric acid as feed stock for commercial blasting agents.

10. The method of claim 1, wherein said recovering comprises recovering at least 90 weight percent of the nitramine.

11. The method of claim 1, wherein the nitramine comprises at least one member selected from the group consisting of 1,3,5,7-tetranitro-1,3,5,7-tetraaza-cyclooctane (HMX), 1,3,5-trinitro-1,3,5-triaza-cyclohexane (RDX), 4,10-dinitro-2,6,8,12-tetraoxa-4,10-diazatetracyclo-[5.5.0.0$^{5,9}$0$^{3,11}$]-dodecane) (TEX), and 2,4,6,8,10,12-hexanitro-2,4,6,8,10,12-hexaazatetracyclo[5.5.0.0$^{5,9}$0$^{3,11}$]-dodecane (CL-20).

12. A method of recovering 1,3,5,7-tetranitro-1,3,5,7-tetraaza-cyclooctane (HMX) from an aluminized energetic material, said method comprising subjecting the aluminized energetic material comprising aluminum, HMX, and at least one binder to treatment in aqueous nitric acid to digest the binder into solution while neither solvating nor solvolyzing into solution at least substantially all of the HMX, and recovering at least a portion of the HMX, wherein a weight ratio of the aqueous nitric acid to the aluminized energetic material in the treatment is in a range of about 4:1 to about 6:1, and further wherein not more than 55 weight percent of the aqueous nitric acid consists of nitric acid.

13. The method of claim 12, wherein the aluminized energetic material further comprises at least one plasticizer, and wherein the treatment of the aluminized energetic material further comprises digesting the plasticizer into solution.

14. The method of claim 12, wherein the aluminized energetic material further comprises at least one plasticizer and at least one inorganic oxidizer, and wherein the treatment of the aluminized energetic material further comprises digesting the plasticizer and the inorganic oxidizer into solution.

15. The method of claim 12, wherein at least 5 weight percent of the aqueous nitric acid consists of nitric acid.

16. The method of claim 12, wherein at least 20 weight percent of the aqueous nitric acid consists of nitric acid.

17. The method of claim 12, wherein at least 35 weight percent of the aqueous nitric acid consists of nitric acid.

18. The method of claim 12, wherein the treatment of the aluminized energetic material comprises neither solvating nor solvolyzing at least 98% of the HMX of the aluminized energetic material into solution.

19. The method of claim 12, wherein the treatment of the aluminized energetic material comprises neither solvating nor solvolyzing at least 99% of the HMX of the energetic material into solution.

20. The method of claim 12, further comprising using digested portions of the energetic material and residual nitric acid as feed stock for commercial blasting agents.

21. The method of claim 12, wherein said recovering comprises recovering at least 90 weight percent of the HMX.

* * * * *

UNITED STATES PATENT AND TRADEMARK OFFICE
CERTIFICATE OF CORRECTION

PATENT NO. : 6,610,156 B2
DATED : August 26, 2003
INVENTOR(S) : Kirstin F. Warner, Louis F. Cannizzor and Robert M. Hajik It is certified that error appears in the above-identified patent and that said Letters Patent is hereby corrected as shown below:

Column 1,
Line 52, change "explosive;" to -- explosive, --

Column 5,
Lien 19, change "are" to -- art --

Column 7,
Line 3, delete "1-"

Column 9,
Line 26, change "50C" to -- 50°C --

Signed and Sealed this

Twenty-first Day of June, 2005

JON W. DUDAS
*Director of the United States Patent and Trademark Office*